United States Patent
Fu et al.

(10) Patent No.: US 9,826,911 B2
(45) Date of Patent: Nov. 28, 2017

(54) WEARABLE DEVICE AND DETERMINATION METHOD THEREOF

(71) Applicant: MediaTek Inc., Hsin-Chu (TW)

(72) Inventors: Chih-Ming Fu, Hsinchu (TW); Shu-Yu Hsu, Taipei (TW); Po-Wen Ku, Jhubei (TW)

(73) Assignee: MEDIATEK INC., Hsin-Chu (TW)

( * ) Notice: Subject to any disclaimer, the term of this patent is extended or adjusted under 35 U.S.C. 154(b) by 0 days.

(21) Appl. No.: 15/167,734

(22) Filed: May 27, 2016

(65) Prior Publication Data

US 2016/0354000 A1 Dec. 8, 2016

Related U.S. Application Data

(60) Provisional application No. 62/172,345, filed on Jun. 8, 2015.

(51) Int. Cl.
| | |
|---|---|
| A61B 5/11 | (2006.01) |
| A61B 5/00 | (2006.01) |
| A61B 5/024 | (2006.01) |
| A61B 5/0402 | (2006.01) |

(52) U.S. Cl.
CPC ........ *A61B 5/02416* (2013.01); *A61B 5/0004* (2013.01); *A61B 5/02405* (2013.01); *A61B 5/02438* (2013.01); *A61B 5/0402* (2013.01); *A61B 5/681* (2013.01); *A61B 5/721* (2013.01); *A61B 5/746* (2013.01); *A61B 5/7455* (2013.01)

(58) Field of Classification Search
CPC ......... A61B 5/024; A61B 5/0408; A61B 5/00; A61B 5/11; A61B 5/7275; A61B 5/6801; A61B 5/02125; A61B 5/4076; A61B 5/02416; A61B 5/0219
USPC ................................ 600/384, 483, 500, 513
See application file for complete search history.

(56) References Cited

U.S. PATENT DOCUMENTS

| | | | |
|---|---|---|---|
| 2014/0276123 A1* | 9/2014 | Yang .................... | A61B 5/7275 600/483 |
| 2016/0073914 A1* | 3/2016 | Lapetina .............. | A61B 5/6824 600/384 |

\* cited by examiner

*Primary Examiner* — Carl H Layno
*Assistant Examiner* — Jon Eric C Morales
(74) *Attorney, Agent, or Firm* — McClure, Qualey & Rodack, LLP

(57) ABSTRACT

A wearable device is provided. The wearable device includes a photon sensor, a processor, and an output unit. The photon sensor senses light reflected from a specific region and transforms the sensed light to a plurality of electric-signal components. The processor receives the electric-signal components sensed within a period to form a dimensional sensing signal. The processor extracts a feature of a waveform of the dimensional sensing signal and determines whether a predetermined heart condition of the object is present according to the feature of the waveform of the dimensional sensing signal to generate a determination signal. The output unit is coupled to the processor. The output unit receives the determination signal and generates an alarm signal according to the determination signal.

19 Claims, 6 Drawing Sheets

WEARABLE DEVICE AND DETERMINATION METHOD THEREOF

CROSS REFERENCE TO RELATED APPLICATIONS

This application claims the benefit of U.S. Provisional Application No. 62/172,345, filed on Jun. 8, 2015, the contents of which are incorporated herein by reference.

BACKGROUND OF THE INVENTION

Field of the Invention

The invention relates to a wearable device, and more particularly to a wearable device which can measure the wearer's heartbeat.

Description of the Related Art

Atrial fibrillation is an abnormal heart rhythm characterized by a rapid and irregular heartbeat. Atrial fibrillation increases the risk of blood clots, stroke, heart failure, and other heart-related complications. Many heart monitors have been developed to detect irregular heartbeat. However, irregular heartbeats occur only rarely. Therefore, most of the time, users do not know when to use these heart-condition monitoring devices to check their heartbeat.

Thus, it is desired to provide a wearable device which can be worn on the user's wrist to monitor his heartbeat all day, and which can issue an alarm signal or message when an irregular heartbeat is detected.

BRIEF SUMMARY OF THE INVENTION

An exemplary embodiment of a wearable device is provided. The wearable device comprises a photon sensor, a processor, and an output unit. The photon sensor senses light reflected from the specific region of an object and transforms the sensed light to a plurality of electric-signal components. The processor receives the electric-signal components sensed within a period to form a dimensional sensing signal. The processor extracts a feature of a waveform of the dimensional sensing signal and determines whether a predetermined heart condition is present according to the feature of the waveform of the dimensional sensing signal to generate a determination signal. The output unit is coupled to the processor. The output unit receives the determination signal and generates an alarm signal according to the determination signal.

Another exemplary embodiment of a determination method for detecting a predetermined heart condition of an object is provided. The determination method comprising the steps of: sensing light reflected from a specific region of the object; transforming the sensed light to a plurality of electric-signal components, wherein the electric-signal components sensed within a period form a dimensional sensing signal; extracting a feature of a waveform of the dimensional sensing signal; determining whether a predetermined heart condition of the object is present according to the feature of the waveform of the dimensional sensing signal to generate a determination signal; and generating an alarm signal according to the determination signal A detailed description is given in the following embodiments with reference to the accompanying drawings.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
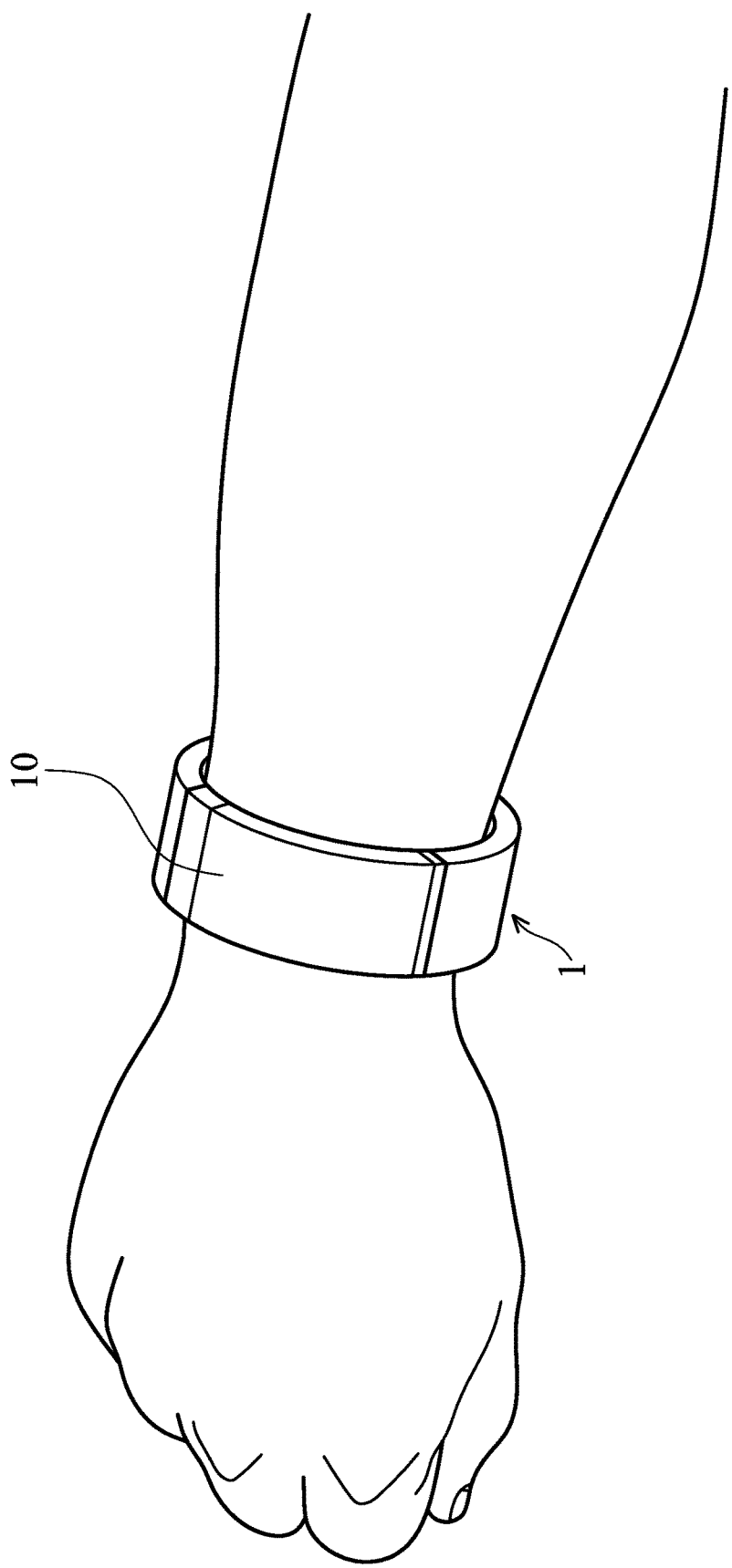
FIG. 1 shows the appearance of an exemplary embodiment of a wearable device.
Figure 2:
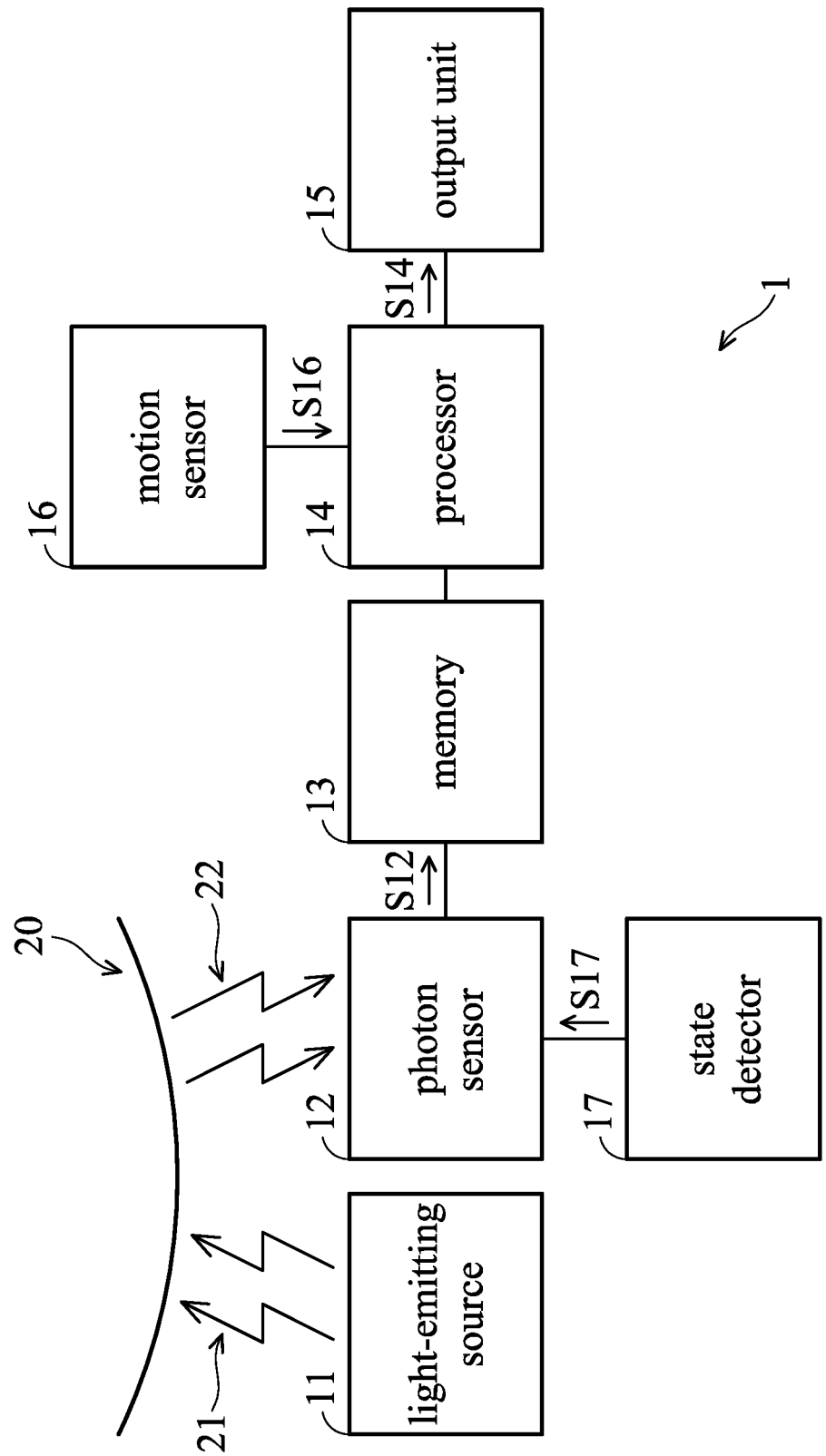
FIG. 2 is a schematic block diagram of an exemplary embodiment of the wearable device in FIG. 1.

FIG. 1 shows the appearance of an exemplary embodiment of a wearable device. Referring to FIG. 1, a wearable device 1 comprises a band 10. The wearable device 1 can be tied onto a specific region of an object through the band 10. In the embodiment, the object is human body (that is, the user of the wearable device 1), and the specific region is one wrist of the user, for example the right wrist. FIG. 2 is a schematic block diagram of the wearable device in FIG. 1. Referring to FIG. 2, the wearable device 1 further comprises a light-emitting source 11, a photon sensor 12, a memory 13, a processor 14, an output unit 15, a motion sensor 16, and a state detector 17. The components 11-17 of the wearable device 1 shown in FIG. 2 are disposed on the band 10. The schematic block diagram in FIG. 2 is used to illustrate the operation of the components 11-17 and show the communication between the components 11-17. The component arrangement shown in FIG. 2 is not the actual arrangement on the band 10. The actual arrangement of the components 11-17 on the band 10 is determined according to the design requirement of the wearable device 1, such as the width and length of the band 10, without limitation to the invention. For illustration, FIG. 2 also shows the specific region 20 of the object.

Referring to FIG. 2, when the wearable device 1 is tied onto the specific region 20, the wearable device 1 may enter a measurement mode. In the measurement mode, the light-emitting source 11 provides light beams 21 to the specific region 20. At the same time, the photon sensor 12 senses the light 22 reflected from skin in the specific region 20 and transforms the sensed light to electric-signal components S12. In the embodiment, each time the photon sensor 12 obtains one electric-signal component S12, the photon sensor 12 stores the one electric-signal component S12 into the memory 13. According to an embodiment, the light-emitting source 11 continuously provides light beams 21. In another embodiment, the light-emitting source 11 discretely provides light beams 21 for reducing power consumption.

Figure 3A:
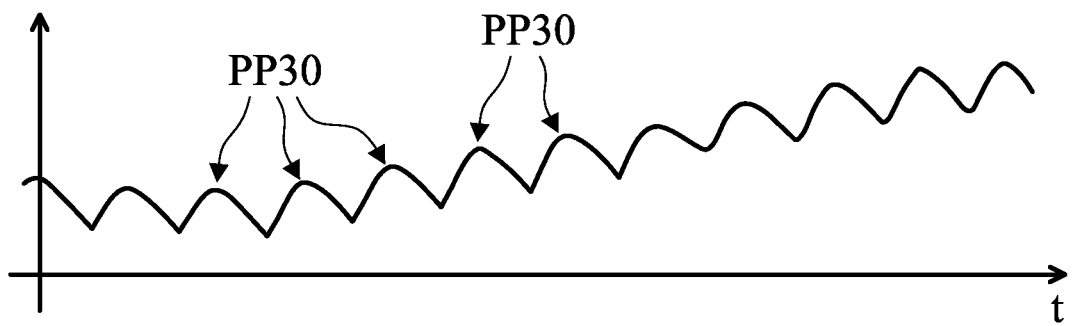
FIG. 3A shows an exemplary embodiment of a dimensional sensing signal which is derived from the light sensed when the heartbeat of an object is regular.
Figure 3B:
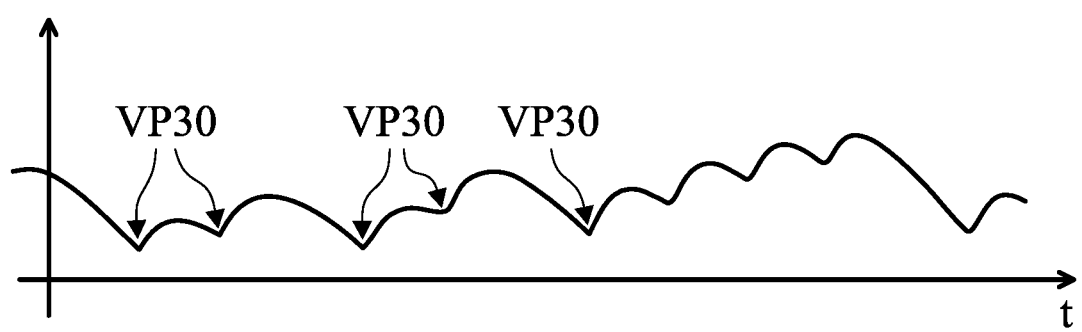
FIG. 3B shows an exemplary embodiment of a dimensional sensing signal which is derived from the light sensed when the heartbeat of an object is irregular.

The processor 14 is coupled to the memory 13 to read the electric-signal components S12. In the embodiment, the processor 14 receives a series of electric-signal components S12 which are sensed by the photon sensor 12 within a predetermined period of the measurement mode, and the series of electric-signal components form a dimensional sensing signal, as shown in FIGS. 3A and 3B. FIG. 3A shows an exemplary embodiment of the dimensional sensing signal S30 which is derived from the light sensed when the heartbeat of the object is regular. FIG. 3B shows an exemplary embodiment of the dimensional sensing signal S31 which is derived from the light sensed when the heartbeat of the object is irregular. It has been known that the heartbeat of the human body affects the volume of blood flow in the wrist. Due to the characteristics of the light absorption of the blood, the intensity of the light sensed by the photon sensor 12 varies with the volume of the blood flow which appears at the same time as the light is being sensed. Thus, the dimensional sensing signal derived from the sensed light can show the condition of the heartbeat of the object. To be more specific, in an embodiment, the period between any two adjacent peak points PP30 of the dimensional sensing signal represents an inter-beat interval, as shown in FIG. 3A. In another embodiment, the period between two adjacent valley points VP30 of the dimensional sensing signal represents an inter-beat interval, as shown in FIG. 3B. In other embodiment, the period between two adjacent points at which slopes of the dimensional sensing signal have a largest or smallest value represents an inter-beat interval. In the following, the operation of the wearable device 1 will be described by referring to a dimensional sensing signal S40 (shown in FIG. 4) which appears when the heartbeat of the object is irregular.

Figure 4:
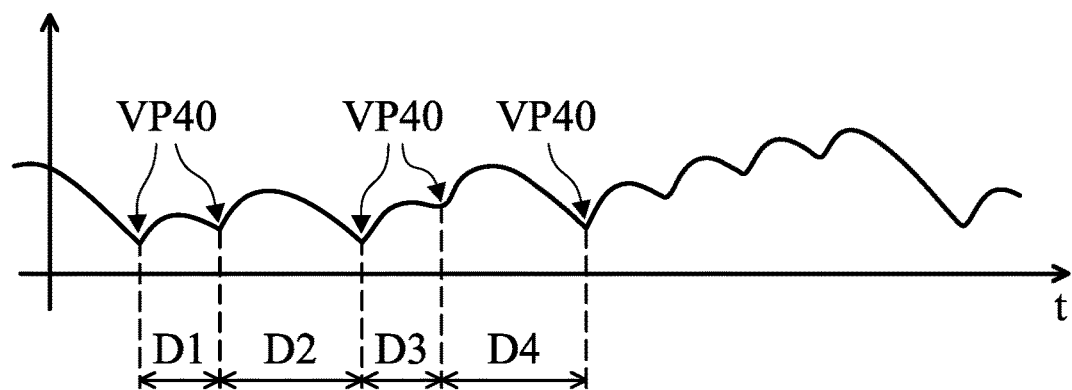
FIG. 4 shows an exemplary embodiment of a dimensional sensing signal whose waveform feature is extracted by the processor of FIG. 2 based on valley points.
Figure 5A:
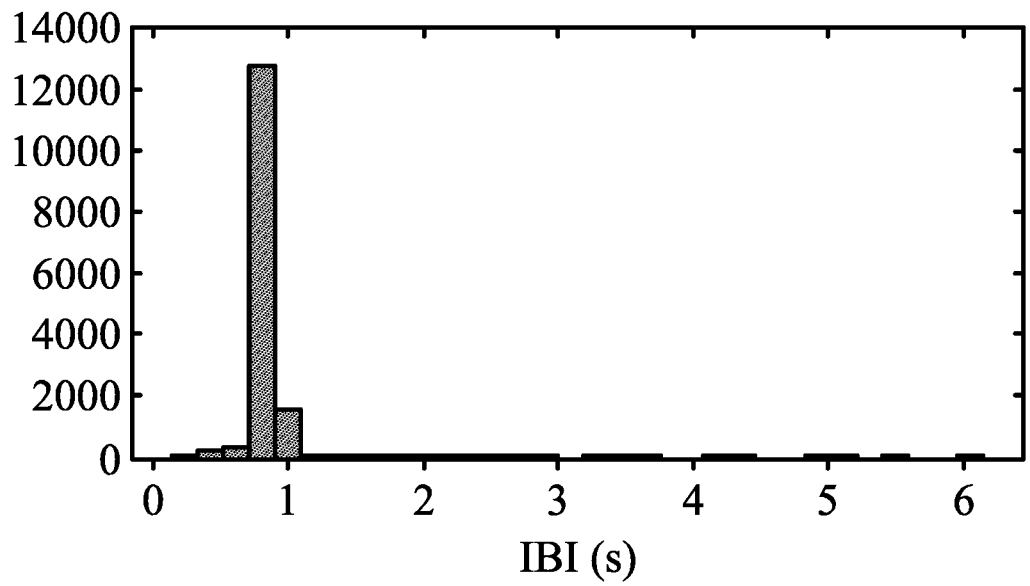
FIG. 5A shows a histogram which is obtained according to statistical information obtained by the processor of FIG. 2 to show standard deviation of inter-beat intervals.
Figure 5B:
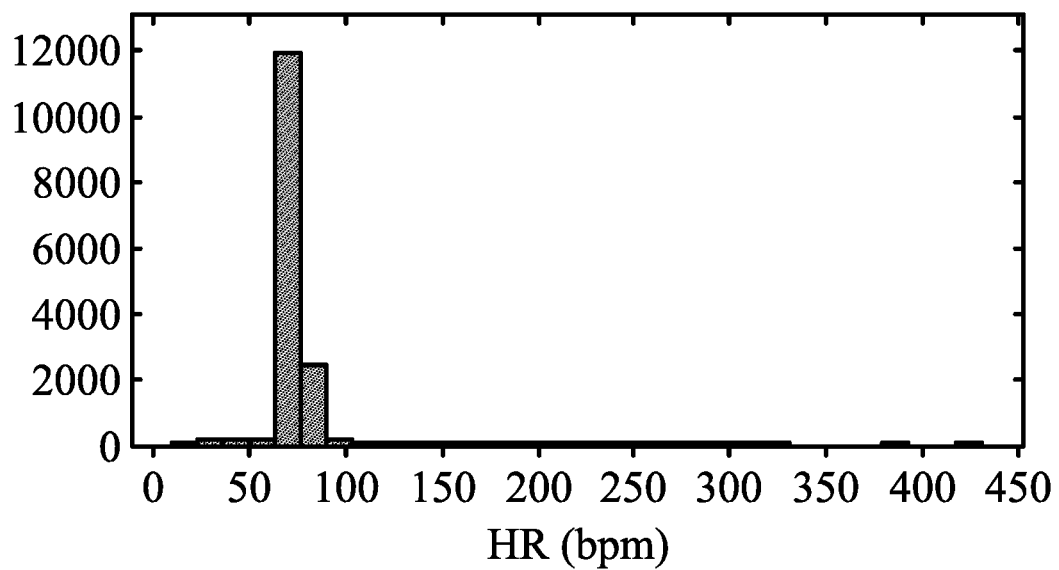
FIG. 5B shows a histogram which is obtained according to statistical information obtained by the processor of FIG. 2 to show variability of the heart rate.

Referring to FIGS. 2 and 4, after obtaining the dimensional sensing signal S40, processor 14 extracts a feature of the waveform of the dimensional sensing signal S40 for determining whether a predetermined heart condition of the object is present according to the feature of the waveform of the dimensional sensing signal S40 to generate a determination signal S14. In the embodiment, the predetermined heart condition is arrhythmia. According to an embodiment, the processor 14 detects feature points of the dimensional sensing signal S40. The feature points of the dimensional sensing signal S40 can be the peak points, the valley points, or the points at which slopes of the dimensional sensing signal S40 have a largest or smallest value. In the following, the valley points VP40 of the dimensional sensing signal S40 are used as an example for illustration. Referring to FIG. 4, the processor 14 calculates the distance D between every two adjacent valley points of the dimensional sensing signal S40 and obtains statistical information of the calculated distances D to serve as the feature of the waveform of the dimensional sensing signal S40. In FIG. 4, only four distances D1-D4 are shown for illustration. In the embodiment, the statistical information is represented by standard deviation, entropy, sample entropy, multi-scale, entropy, a part of power spectrum, histogram, or a multi-dimension vector. Referring to FIG. 5A, a histogram is obtained according to the statistical information related to the calculated distances D to show the standard deviation of the inter-beat intervals. FIG. 5B is a histogram which is obtained according to the statistical information of the calculated distances D to show the variability of the heart rate. After obtaining the statistical information of the calculated distances D, the processor 14 processes the statistical information by applying an algorithm to determine whether the predetermined heart condition (arrhythmia) is present, and generates the determination signal S14 according to the determination result to the output unit 15. In the embodiment, the algorithm comprises a decision rule, decision tree, support vector machine, random forest, or deep learning algorithm.

According to another embodiment, the processor 14 detects a shape of the waveform of the dimensional sensing signal S40 to serve as the feature of the waveform of the dimensional sensing signal S40. After detecting the shape of the waveform of the dimensional sensing signal S40, the processor 14 compares the shape of the waveform of the dimensional sensing signal with a reference shape to determine whether the predetermined heart (arrhythmia) condition is present. When the shape of the waveform of the dimensional sensing signal S40 is different from the reference shape, the processor 14 determines that the predetermined heart condition is present. In an embodiment, the reference shape is defined for a regular heartbeat. In another embodiment, the reference shape is the shape of the dimensional sensing signal which is derived from the light sensed by the photon sensor 12 before the predetermined period of the measurement mode.

For accurately extracting the feature of the waveform of the dimensional sensing signal S40, the processor 14 can process the dimensional sensing signal S40 by a filter for filtering invalid noise.

In cases where the light-emitting source 11 discretely provides light beams 21, when the light-emitting source 11 stops providing the light beams 21, the photon sensor 12 senses the ambient light. The processor uses the electric-signal components related to the sensed light ambient as reference parameters to compensate the dimensional sensing signal S40 for change in the environment lighting condition.

When the processor 14 determines that the predetermined heart condition is present, the output unit 15 generates an alarm signal according to the determination signal S14 from the processor 14 to indicate that the heartbeat of the object is irregular. According to the embodiment, the output unit 15 comprises at least one of a display, a vibration unit, a speaker, and a wireless transmission unit. In an embodiment, when the processor 14 determines that the predetermined heart condition is present, the display shows information related to the predetermined heart condition according to the alarm signal, such as a sign, a message. In another embodiment, when the processor 14 determines that the predetermined heart condition is present, the vibration unit enables a vibration alarm according to the alarm signal to warn the object of the arrhythmia. In another embodiment, when the processor 14 determines that the predetermined heart condition is present, the speaker plays an alarm sound according to the alarm signal to warn the object of the arrhythmia. In an embodiment, when the processor 14 determines that the predetermined heart condition is present, the wireless transmission unit communicates with a remote device according to the alarm signal to enable the remote device to perform a specific measurement. For example, the remote device is an electrocardiography (ECG) recorder. When the processor 14 determines that the predetermined heart condition is present, the wireless transmission unit enables the ECG recorder to perform an ECG measurement operation.

According to the above embodiments, the wearable device 1 can be tied onto the specific region (wrist) of the object (user) to monitor the heartbeat of the user all day and issue an alarm signal or message when an irregular heartbeat is detected. When the user is notified by the alarm signal, the user or the user's doctor may infer that atrial fibrillation may be occurring. Then, in response to the alarm signal, the user or her doctor may take action, such as ECG measurement, or diagnosis of a heart disease.

In an embodiment, the light-emitting source 11 is implemented by a light-emitting diode. The intensity of the light beams provided by the light-emitting source 11 is adjustable. For example, at the beginning of the measurement mode, the light-emitting source 11 provides light beams and adjusts the intensity of the light beams, so that the entire intensity of the light sensed by the photon sensor 12 is increased. Thus, the amplitude of the dimensional sensing signal derived from the sensed light is relatively greater or more clear, which is beneficial for the processor 14 to accurately determine whether the predetermined heart condition (arrhythmia) is present based on the feature of the waveform of the dimensional sensing signal.

In some embodiments, when the object moves violently, the entire intensity of the light sensed by the photon sensor 12 may become excessive great or small, which cannot reflect the condition of the heartbeat of the object. Thus, any electric-signal components which are transformed from the light sensed while the object is moving violently are invalid for the determination of arrhythmia. Referring to FIG. 2, the wearable device 1 also comprises a motion sensor 16. The motion sensor 16 is used to sense the motion of the object. When the motion sensor 16 senses that the object is moving violently, the motion sensor 16 generates an indication signal S16 to the processor 14. When the processor 14 receives the indication signal, the processor 14 excludes the electric-signal component, which is transformed from the light sensed during the violent movement of the object, from the dimensional sensing signal.

When the object is sleeping, the entire intensity of the light sensed by the photon sensor 12 may not be affected by larger motion, and the processor 14 may accurately determine whether the predetermined heart condition (arrhythmia) is present. Thus, the wearable device 1 also comprises a state detector 17. The state detector 17 is used to detect the current state of the object. When the state detector 17 detects that the object is in a specific state (such as a sleeping state), the state detector 17 generates an enable signal S17 to trigger the photon sensor 12 to sense the light from the specific region. Note that the input of state detector 17 can be the output of processor 14. In an embodiment, the detection of the specific state can be performed by the motion sensor 16. In this case, the state detector 17 is removed from the wearable device 1. When the motion sensor 16 senses that the object does not move for a long time, the motion sensor 16 determines that the object is in the specific state (sleeping state) and generates an enable signal to trigger the photon sensor 12.

Figure 6:
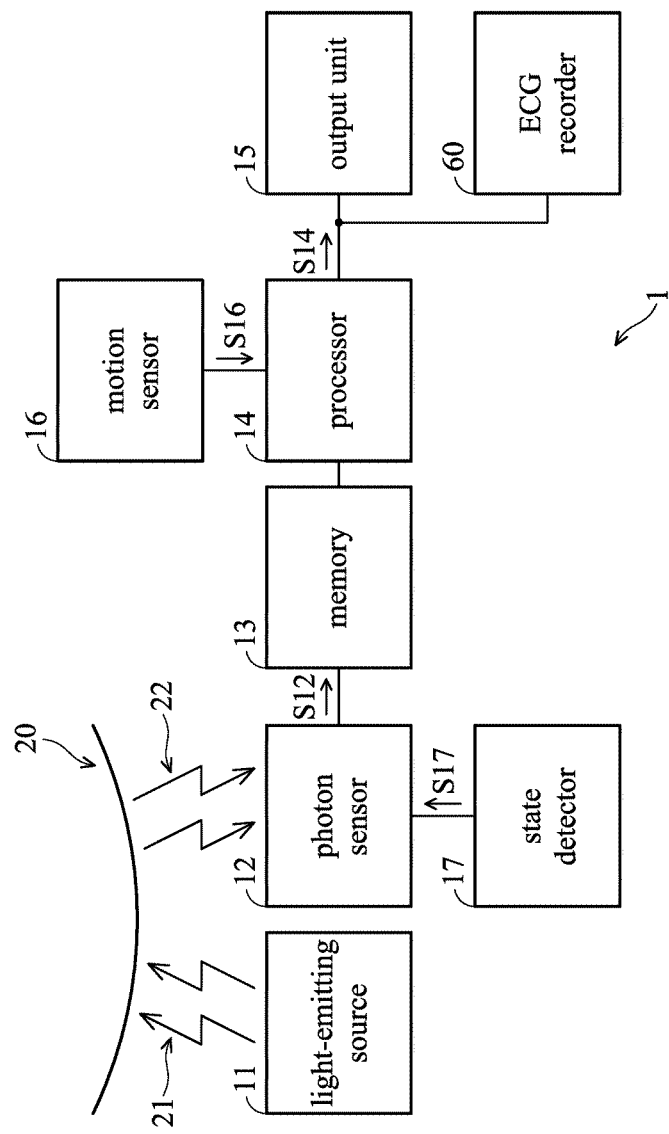
FIG. 6 is a schematic block diagram of another exemplary embodiment of the wearable device in FIG. 1.

In some embodiments, the wearable device 1 further comprises an ECG recorder 60, as shown in FIG. 6. The ECG recorder 60 is disposed on the band 10. When the wearable device 1 is tied on the specific region (wrist) of the object (user), the electrodes of the ECG recorder contact the skin in the specific region. The ECG recorder 60 is coupled to the processor 14. When the processor 14 determines that the predetermined heart condition (arrhythmia) is present, the determination signal S14 from the processor 14 is generated to trigger the ECG recorder 60 to perform an ECG measurement operation, so that atrial fibrillation can be confirmed according to the results of the ECG measurement. In response to the ECG measurement being finished, the ECG recorder 60 transmits ECG measurement data representing the measurement results to a server or receiver. Moreover, the ECG recorder 60 also transmits the ECG measurement data to the processor 14. The processor 14 determines whether or not arrhythmia is present according to the ECG measurement data, and generates a signal according to the determination result. The signal may be transmitted to the output unit 15. In this case, the output unit 15 can generate the alarm signal according to the signal related to the ECG measurement.

While the invention has been described by way of example and in terms of the preferred embodiments, it is to be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A wearable device comprising:
   a photon sensor sensing light reflected from a specific region of an object and transforming the sensed light to a plurality of electric-signal components;
   a processor receiving the electric-signal components obtained within a period to form a dimensional sensing signal, detecting a plurality of feature points of the dimensional sensing signal, calculating a distance between two adjacent feature points among the plurality of feature points, extracting a feature of a waveform of the dimensional sensing signal according to the calculated distance, and determining whether a predetermined heart condition of the object is present according to the feature of the waveform of the dimensional sensing signal to generate a determination signal; and
   an output unit, coupled to the processor, receiving the determination signal and generating an alarm signal according to the determination signal.

2. The wearable device as claimed in claim 1, wherein when the processor determines that the predetermined heart condition is present, the output unit generates the alarm signal according to the determination signal to indicate that heartbeat of the object is irregular.

3. The wearable device as claimed in claim 1, wherein the output unit comprises a display to show information related to the predetermined heart condition according to the alarm signal, a vibration unit to enable a vibration alarm according to the alarm signal, a speaker to play an alarm sound according to the alarm signal, or a wireless transmission unit to communicate with a remote device according to the alarm signal.

4. The wearable device as claimed in claim 1, wherein the processor obtains statistical information of the calculated distance to serve as the feature of the waveform of the dimensional sensing signal.

5. The wearable device as claimed in claim 4, wherein the processor process the statistical information by applying an algorithm to determine whether the predetermined heart condition is present.

6. The wearable device as claimed in claim 1 further comprising:
   a band, wherein the photo sensor, the processor, and the output unit are disposed on the band, and the wearable device is tied onto the specific region through the band.

7. The wearable device as claimed in claim 1 further comprising:
   a light-emitting source providing light beams to the specific region, wherein the photon sensor senses the light reflected from the specific region being illuminated by the light beams.

8. The wearable device as claimed in claim 1, wherein intensity of the light beams provided by the light-emitting source is adjustable.

9. The wearable device as claimed in claim 1 further comprising:
an electrocardiography recorder, coupled to the processor,
wherein when the processor determines that the predetermined heart condition is present, the processor generates the determination signal to trigger the ECG recorder to perform an ECG measurement operation.

10. The wearable device as claimed in claim 1, further comprising:
a motion sensor, coupled to the processor, sensing motion of the object,
wherein when the motion sensor senses that the object moves violently, the processor excludes at least one electric-signal component which is transformed from the light sensed during violent movement of the object from the dimensional sensing signal.

11. A determination method for a predetermined heart condition of an object, comprising:
sensing light reflected from a specific region of the object;
transforming the sensed light to a plurality of electric-signal components, wherein the electric-signal components sensed within a period form a dimensional sensing signal;
detecting a plurality of feature points of the dimensional sensing signal;
calculating a distance between two adjacent feature points among the plurality of feature points;
extracting a feature of a waveform of the dimensional sensing signal according to the calculated distance;
determining whether a predetermined heart condition of the object is present according to the feature of the waveform of the dimensional sensing signal to generate a determination signal; and
generating an alarm signal according to the determination signal.

12. The determination method as claimed in claim 11, wherein when the processor determines that the predetermined heart condition is present, the alarm signal is generated to indicate that heartbeat of the object is irregular.

13. The determination method as claimed in claim 11 further comprising:
according to the alarm signal, showing information related to the predetermined heart condition, enabling a vibration alarm, playing an alarm sound, or communicating with a remote device.

14. The determination method as claimed in claim 11, wherein the step of extracting the feature of the waveform of the dimensional sensing signal comprises:
obtaining statistical information of the calculated distance to serve as the feature of the waveform of the dimensional sensing signal.

15. The determination method as claimed in claim 14, wherein the step of determining whether the predetermined heart condition of the object is present comprises:
processing the statistical information using an algorithm to determine whether the predetermined heart condition is present.

16. The determination method as claimed in claim 11 further comprising:
providing light beams to the specific region,
wherein in the step of sensing light reflected, the light reflected from the specific region being illuminated by the light beams is sensed.

17. The determination method as claimed in claim 16 further comprising:
adjusting intensity of the light beams.

18. The determination method as claimed in claim 11 further comprising:
when it is determined that the predetermined heart condition is present, triggering an electrocardiography (ECG) recorder according to the determination signal to perform an ECG measurement operation.

19. The determination method as claimed in claim 11 further comprising:
sensing motion of the object,
wherein when it is sensed that the object moves violently, at least one electric-signal component sensed during the violent movement of the object is excluded from the dimensional sensing signal.

* * * * *